United States Patent [19]

Lambrecht et al.

[11] Patent Number: 4,479,931
[45] Date of Patent: Oct. 30, 1984

[54] METHOD FOR NON-INVASIVE DETECTION OF OCULAR MELANOMA

[75] Inventors: Richard M. Lambrecht, Quogue; Samuel Packer, Floral Park, both of N.Y.

[73] Assignee: The United States of America as represented by the United States Department of Energy, Washington, D.C.

[21] Appl. No.: 422,511

[22] Filed: Sep. 23, 1982

[51] Int. Cl.³ .............................................. A61K 49/00
[52] U.S. Cl. ..................................... 424/1.1; 128/659; 378/205; 424/9
[58] Field of Search ...................... 424/1.1, 9; 378/205; 128/659

[56] References Cited

U.S. PATENT DOCUMENTS

| | | | |
|---|---|---|---|
| 3,863,623 | 2/1975 | Trueblood et al. | 128/2 A |
| 3,893,447 | 7/1975 | Hochheimer et al. | 128/2 A |
| 3,997,793 | 12/1976 | Rogers et al. | 378/205 |
| 4,245,646 | 1/1981 | Ionnou et al. | 128/653 |

OTHER PUBLICATIONS

Packer et al., "Non-Invasive Nuclear Detection of Choroidal Melanoma", Int. Symp. Intraocular Tumors, Schwerin, E. Germany, May, 1981, (inpress).
Medical Radio Isotope Scintigraphy 1972, IAEA, Viena, 1972, vol. I, pp. 2-4 of Contents; vol. 2, pp. 497-518.
Packer et al., Chemical Abstracts, vol. 88 (1978), #18327p, CRC Manual of Nuclear Medicine Procedures, J. W. Keys, ed., 3rd., 1978, CRC Press, Inc., W. Palm Beach, pp. 109-110.
New Techniques in Tumor Location and Radio Immunoassay, M. N. Croll et al., eds., J. Wiley & Sons, N.Y., 1974, pp. 165-170.

Primary Examiner—Christine M. Nucker
Attorney, Agent, or Firm—Vale P. Myles; James W. Weinberger; Michael F. Esposito

[57] ABSTRACT

There is described an apparatus and method for diagnosing ocular cancer that is both non-invasive and accurate which comprises two radiation detectors positioned before each of the patient's eyes which will measure the radiation level produced in each eye after the administration of a tumor-localizing radiopharmaceutical such as gallium-67.

9 Claims, 2 Drawing Figures

METHOD FOR NON-INVASIVE DETECTION OF OCULAR MELANOMA

BACKGROUND OF THE INVENTION

The United States Government has rights in this invention pursuant to Contract Number DE-AC02-76CH00016, between the U.S. Department of Energy and Associated Universities, Inc.

The subject invention relates to the detection of cancerous tumors. More particularly, it relates to a method and apparatus for using radiopharmaceuticals to detect ocular tumors.

Currently, the final diagnosis of ocular tumors may be based upon measurement of the uptake of phosphorus-32 in the eye. Phosphorus-32 decays by beta emission. The absorbed radiation dose to the patient undergoing the phosphorus-32 test is excessive, i.e., 20–30 Rads to bone per test. Further, the beta radiation cannot be detected outside the body and it is necessary for a physician to perform a surgical procedure in order that a small probe can be placed on the surface of the eye and the radioactivity recorded. The decision as to whether or not the eye has a malignancy is based on the detection of increased radioactive uptake in the area of the tumor as well as other diagnostic procedures employed by the physician.

The recent development of radiopharmaceuticals based on nuclides such as gallium-67, iodine-123, iodine-125 and fluorine-18 have sparked an effort to develop accurate, non-invasive techniques for diagnosis of ocular cancers. One such technique is the dual pin-hole collimator for gamma cameras, described in Blanquet, et al., "Ocular Scintigraphy", *Nuclear Ophthalmology*, Ed. Croll, et al., J. Wiley and Sons, New York, 1976. Another is the ultrasound guided probe, described in Weinstock, et al., "An Ultrasonic Guided Gamma Probe for Intraocular Melanoma Detection", *Nuclear Ophthalmology*, Ed. Croll, et al., J. Wiley and Sons, New York, 1976. These techniques, however, share certain problems. They require relatively expensive equipment and sophisticated operating techniques and so are not suited for clinical or mass-screening applications.

Thus, it is an object of the present invention to provide an apparatus and method for diagnosing ocular cancer that is both non-invasive and accurate.

It is another object of the present invention to provide such an apparatus and method that are suitable for clincial and mass-screening applications.

It is still another object of the present invention to provide an apparatus and method for detecting ocular cancer which will minimize the exposure of the patient to radiation.

BRIEF SUMMARY OF THE INVENTION

The above objects are achieved and the disadvantages of the prior art are overcome by an apparatus for diagnosing ocular cancer which comprises two radiation detectors and means for mounting the two detectors. The mounting means further comprises means for adjusting the positioning of the detectors so that one may be positioned before each of the eyes of a subject so that each detector will measure the radiation level in its associated eye under substantially identical conditions. Preferably, the detectors are collimated so as to substantially reduce their exposure to radiation from sources other than their associated eyes.

The above described apparatus is used to diagnose ocular cancer in the following way. First, the tumor-localizing radiopharmaceutical is administered to a subject. Preferably, the radiopharmaceutical is chosen from the group consisting of gallium-67, iodine-123, iodine-125 and fluorine-18 radiopharmaceuticals and still more preferably the radiopharmaceutical is gallium-67 citrate. After administering the radiopharmaceutical the above described apparatus is used to simultaneously measure the level of radiation in each of the patient's eyes. These levels are then compared so that the presence of a tumor in one eye may be determined by the higher level of radioactivity in the diseased eye. In one embodiment the levels of radioactivity are measured in terms of a preselected radioactive standard.

Thus, it may be seen that the subject invention advantageously provides an inexpensive apparatus and a method for using this apparatus in the diagnosis of ocular cancer, and that this apparatus and method are suitable for clinical and mass-screening applications.

It is another advantage of the subject invention that the diagnostic test is non-invasive and simple to perform and does not require highly sophisticated personnel to administer the test.

It is still another advantage of the present invention that the subject is exposed to a lower level of radiation than with other known non-invasive techniques for the diagnosis of ocular cancer.

Other objects and advantages of the subject invention will be apparent to those skilled in the art from consideration of the attached drawings and the detailed description set forth below.

DETAILED DESCRIPTION OF EMBODIMENTS OF THE INVENTION

Figure 1:
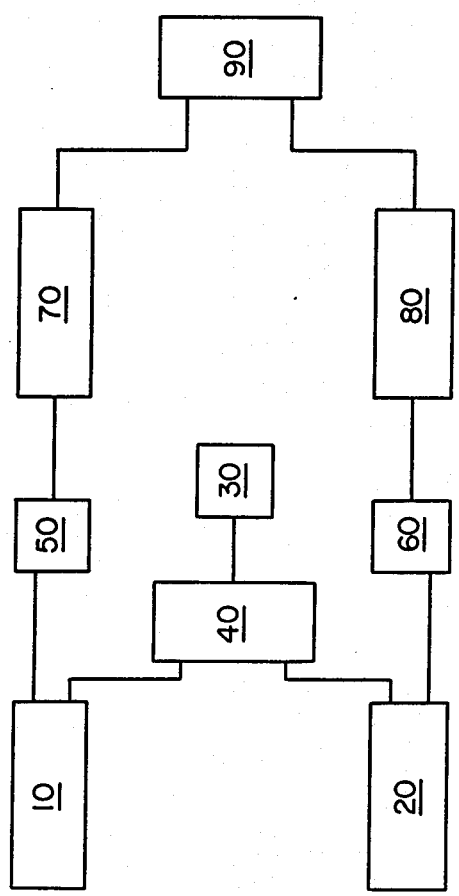
FIG. 1 is a schematic block diagram of an apparatus in accordance with the present invention.

Turning to FIG. 1, there is shown a schematic block diagram of an apparatus in accordance with the subject invention. Collimated detectors 10 and 20 are mounted on a fixture (not shown) so that they may be steadily positioned before the eyes of a subject. Preferred detectors for the purposes of the apparatus of the present invention are one inch sodium iodide (NaI(T) detectors collimated to have a one-half inch window so that each detector responds substantially only to the radiation of its associated eye. Additional shielding may be used to further reduce the exposure of the detectors to background radiation. Collimated detectors suitable for use as components 10 and 20 are commercially available and may be purchased, for example, from Technical Associates, Inc. of Canoga Park, Calif. Detectors 10 and 20 are powered by a high voltage power supply 30, which may be a Canberra Industries Model 3102 power supply, through a conventional voltage divider circuit 40 which is used to equalize the responses of detectors 10 and 20.

The output of detectors 10 and 20 is connected to preamplifiers 50 and 60, which may be Canberra Industries Model 2005 scintillation preamplifiers, which are in turn connected to amplifier-analyzers 70 and 80, which may be Canberra Industries Model 2015 Amplifier-timing Single Channel Amplifiers. Amplifier-analyzers 70 and 80 discriminate signals from detectors 10 and 20 which have the appropriate magnitude to represent responses to the radiation produced by the radiopharmaceutical and produce an output only in response to those signals. The outputs of amplifier-analyzers 70 and 80 are connected to dual counter 90, which may be Canberra Industries Model 1776 Dual Counter Timer. Thus, the apparatus shown will provide two counts, each substantially proportional to the radiation induced in one of the subject's eyes by the previously administered tumor-localizing radiopharmaceutical.

It should be noted that all of the components used in the apparatus of the subject invention are conventional and numerous equivalents are readily commercially available. The apparatus of the subject invention may be constructed from any of the numerous commercial equivalents without departing from the scope of the invention.

The above described apparatus is used in the method of the subject invention as follows:

A tumor-localizing radiopharmaceutical is administered to a subject sometime prior to the test. The precise quantities of radiopharmaceutical administered and the precise timing of its administration will vary with the radiopharmaceutical chosen and may be determined in accordance with known principles by those skilled in the field of nuclear medicine. Preferably, the radiopharmaceutical used is gallium-67 citrate administered 48 to 72 hours prior to the test.

Immediately prior to the test the detectors are calibrated using a standard source of known activity. Where gallium-67 citrate is administered as described above, a ten millicurie gallium-67 source may be used as the standard.

Figure 2:
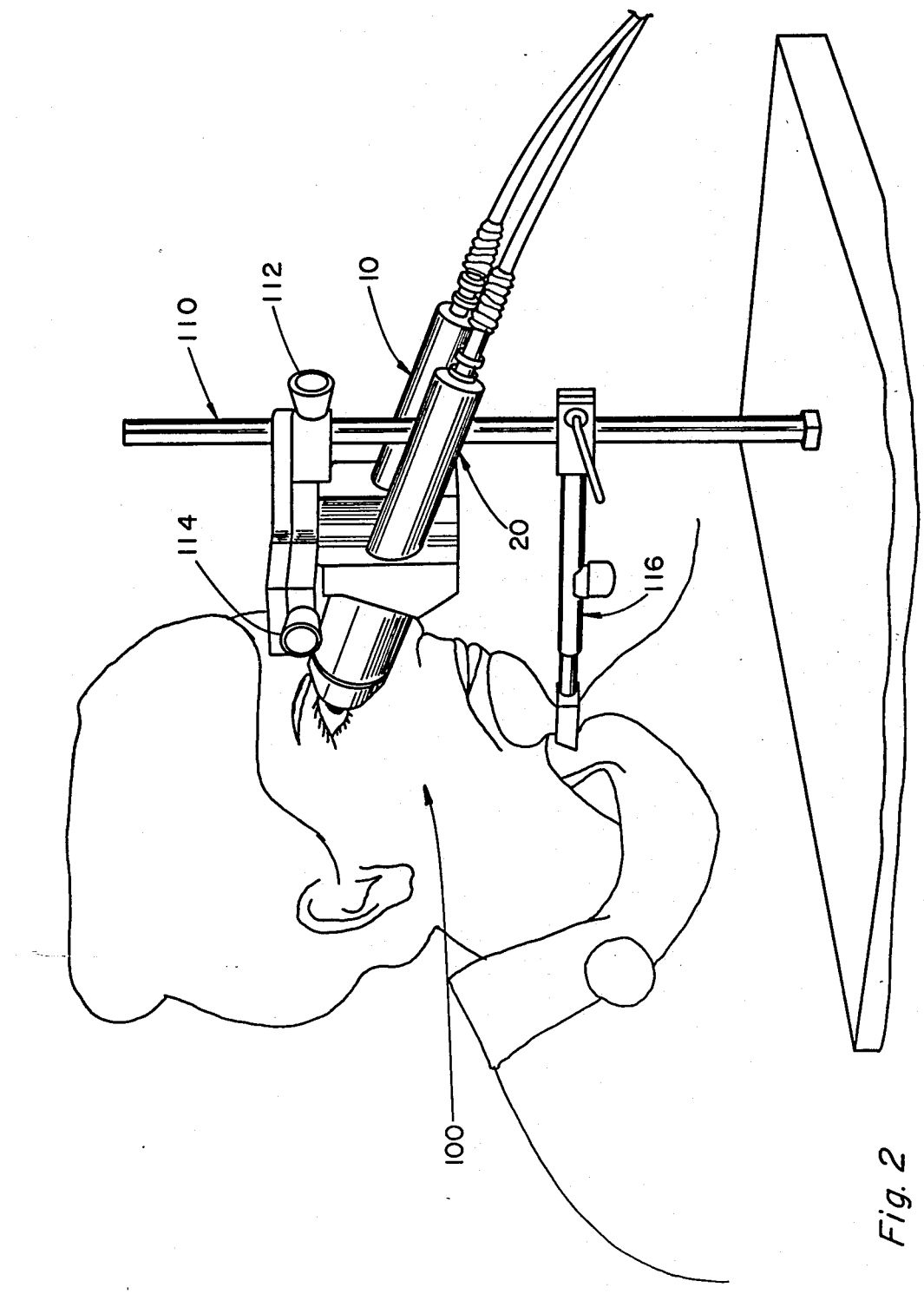
FIG. 2 is a perspective view of an apparatus in accordance with the subject invention used in accordance with the method of the subject invention.

The test is conducted, as may be seen in FIG. 2, by having the subject 100 place his or her eyes (open or closed) directly in front of the openings in collimated detectors 10 and 20 and simultaneously counting the radiation levels obtained in each eye for a predetermined period. The appropriate counting period will vary with the particular radiopharmaceutical chosen and may be determined by known procedures by those skilled in the art of nuclear medicine. Where gallium-67 citrate is administered as the radiopharmaceutical, as described above, a period of 60 to 120 seconds may be used.

The radiation levels are normalized to the standard and any substantial positive differential in the normalized radiation levels of one eye with respect to the other may be taken as indicative of the presence of a tumor in that eye.

To aide subject 100 to maintain a steady position during the counting period, detectors 10 and 20 are mounted in a fixture 110 having a head support 116. Fixture 110 is also provided with adjustments 112 and 114 to allow vertical and independent horizontal positioning of detectors 10 and 20.

EXPERIMENTAL EXAMPLE

Table I sets forth the results of tests performed to evaluate the effectiveness and accuracy of the method and apparatus of the subject invention. Eleven subjects known to have tumors in one eye were tested. Presence of tumors was confirmed by pathology, after a decision to excise the eye resulted from diagnosis by other conventional methods. 5.0 millicuries of gallium-67/citrate was administered intravenously to each subject approximtely 48-72 hours prior to testing. Immediately prior to the test each of the detectors was calibrated using a 10 microcuries gallium-67 source. The subject was seated with one eye against each of the collimated detectors. The activity in each eye was measured for 60-120 seconds and was expressed as a percentage of the response by the associated detector to the gallium-67 source. For the purposes of this evaluation, tests showing the tumorous eye to have the greater activity were classified as positive, while tests showing the non-tumorous eye to have the greater activity were classified as negative.

Of the eleven subjects tested, four had negative results. It is suggested that three of these negative results were due to the fact that the subjects' tumors had previously been treated with radiation therapy, and it is not yet known whether gallium-67 is specific or nonspecific for radiation-treated tumors. The other negative result is anomalous is that there is no apparent explanation for the negative result.

This experiment shows the usefulness of the method and apparatus of the subject invention for the detection of ocular tumors. With the development of improved tumor specific radiopharmaceuticals it is anticipated that improved accuracy will be obtained. Table I, which follows, shows the test results for all eleven patients tested using the apparatus and method of the present invention. It also includes information relative to the tumors that were present in each of these patients.

TABLE I

Dual Eye Probe and Gallium-67 Citrate[1]

| Patient | % of Standard Right Eye | Left Eye | Result | Tumor Size (mm) | Treatment or Cell Type |
|---|---|---|---|---|---|
| J. B. | 1.01 | 0.73 | + | 15 × 15 × 8 | Mixed |
| E. P. | 0.76 | 0.29 | + | 15 × 15 × 10 | Mixed |
| W. D. | 0.96 | 0.90 | − | 10 × 10 × 2 | Not Available |
| A. D. | 0.96 | 0.88 | + | 14 × 14 × 7 | Radiation Therapy |
| R. R. | 0.37 | 0.26 | − | 10 × 10 × 5 | Radiation Therapy and Chemotherapy |
| K. S. | 0.39 | 0.29 | + | 15 × 15 × 8 | Not Available |
| M. F. | 0.93 | 0.75 | + | 10 × 10 × 6 | Radiation Therapy |
| W. T. | 0.32 | 0.02 | + | 12 × 12 × 7 | Radiation Therapy |
| A. C. | 0.25 | 0.85 | − | 12 × 10 × 2 | Not Available |
| C. H. | 1.65 | 0.98 | + | 16 × 16 × 10 | Spindle A |

TABLE I-continued

| | Dual Eye Probe and Gallium-67 Citrate[1] | | | | |
|---|---|---|---|---|---|
| Patient | % of Standard Right Eye | Left Eye | Result | Tumor Size (mm) | Treatment or Cell Type |
| J. C.[2] | 1.03 | 1.21 | — | 10 × 10 × 3 | — |

[1] 5.0 mCi gallium-67 citrate I.V. - 48–72 hours to testing
[2] False Negative, Radiation Therapy followed gallium-67 test
Note: Radiation Therapy on above patients, with exception of J. C., was administered prior to gallium-67 test The above description and example and the attached drawings of embodiments of the subject invention are intended to be illustrative only. Other embodiments of the method and apparatus of the subject invention will be readily apparent to those skilled in the art. Thus, the limitations of the subject invention are to be found only in the claims set forth below.

We claim:

1. A method for non-invasively and accurately diagnosing ocular cancer comprising:
   (a) providing two radiation detectors;
   (b) positioning each of said detectors respectively before each of the eyes of a subject so that each detector will measure the radiation level in its associated eye under substantially identical conditions;
   (c) simultaneously measuring and recording the integrated output of each of said detectors, thereby to normalize said measured radiation levels to a preselected standard, whereby a predetermined positive differential recorded for the normalized radiation level of one detector gives an indication of ocular cancer in the eye associated with that detector.

2. A method as described in claim 1, wherein said detector is collimated so as to substantially reduce its exposure to radiation from sources other than the associated eye.

3. A method as described in claim 2, further comprising providing a standard radiation source for periodically calibrating said detectors.

4. A method as described in claim 1, wherein said detectors are chosen to be responsive to radiation from a pre-selected tumor localizing radiopharmaceutical.

5. A method as described in claim 4, wherein said radiopharmaceutical is chosen from a group consisting of gallium-67, iodine-123, iodine-125 and fluorine-18.

6. A method as described in claim 1, wherein said radiopharmaceutical is gallium-67 citrate and said detectors are sodium iodide detectors.

7. A method for detecting ocular cancer comprising the steps of:
   (a) administering a tumor localizing radiopharmaceutical to a subject;
   (b) simultaneously separately measuring the level of radioactivity in each eye of said subject;
   (c) comparing the levels so measured by normalizing each of the measured levels relative to a preselected standard level and by measuring the differential between the normalized levels relating to the respective eyes, whereby a predetermined positive differential in one of the normalized measured levels gives an indication of ocular cancer in the eye showing the positive differential.

8. A method as described in claim 7, wherein said radiopharmaceutical is chosen from a group consisting of gallium-67, iodine-123, iodine-125 and fluorine-18.

9. A method as described in claim 8, wherein said radiopharmaceutical is gallium-67 citrate.

* * * * *